United States Patent
Jednákovits et al.

(10) Patent No.: US 6,384,029 B1
(45) Date of Patent: May 7, 2002

(54) OPTICALLY ACTIVE PYRIDYL-4H-1,2, 4-OXDADIAZINE DERIVATIVE AND ITS USE IN THE TREATMENT OF VASCULAR DISEASES

(75) Inventors: Andrea Jednákovits, Szentendre; Lászió Ürögdi, Budapest; Lászió Dénes, Budapest; István Kurucz, Budapest; Ede Márványos, Budapest; Mihály Barabás, Budapest; Ernö Bácsy, Budapest; Zsuzsanna Korom, Veszprém; Zoltán Nagy, Budapest; László Ürge, Budapest; Jenö Szilbereky, Budapest; Károly Acsai, Budapest; Péter Krajcsi, Budapest; Zita Csákai, Kunszentmiklós; Magdolna Török, Mátészalka, all of (HU)

(73) Assignee: Biorex Kutató Fejlesztö RT., Veszprém-Szabadságpuszta (HU)

( * ) Notice: Subject to any disclaimer, the term of this patent is extended or adjusted under 35 U.S.C. 154(b) by 0 days.

(21) Appl. No.: 09/762,949
(22) PCT Filed: Dec. 7, 1999
(86) PCT No.: PCT/HU99/00095
 § 371 Date: May 15, 2001
 § 102(e) Date: May 15, 2001

(87) PCT Pub. No.: WO00/35914
 PCT Pub. Date: Jun. 22, 2000

(30) Foreign Application Priority Data
Dec. 14, 1998 (HU) .......................... P 9802897

(51) Int. Cl.[7] ................. C07D 413/04; A61K 31/5395; A61P 9/00
(52) U.S. Cl. ...................... 514/229.2; 544/66
(58) Field of Search ................ 514/229.2; 544/0.66

(56) References Cited
FOREIGN PATENT DOCUMENTS

| WO | WO 97/16439 | * 5/1997 |
| WO | WO 98/06400 | * 2/1998 |

* cited by examiner

*Primary Examiner*—Brenda Coleman
(74) *Attorney, Agent, or Firm*—Finnegan, Henderson, Farabow, Garrett & Dunner, L.L.P.

(57) ABSTRACT

The invention relates to (−)-5,6-dihydro-5-(1-piperidinyl)-methyl-3-(3-pyridyl)-4H-1,2,4-oxadiazine to the therapeutical use thereof and to phamaceutical compositions containing the compounds as active ingredient.

13 Claims, No Drawings

OPTICALLY ACTIVE PYRIDYL-4H-1,2, 4-OXDADIAZINE DERIVATIVE AND ITS USE IN THE TREATMENT OF VASCULAR DISEASES

This is a 371 of PCT/HU99/0095, filed Dec. 7, 1999.

TECHNICAL FIELD

The invention relates to an optically active form of a pyridyl-4H-1,2,4-oxadiazine derivative, to the therapeutical use thereof and to pharmaceutical compositions containing the compound as active ingredient. More particularly, the invention relates to the (−) enantiomer of 5,6-dihydro-5-(1-piperidinyl)-methyl-3-(3-pyridyl)4H-1,2,4-oxadiazine and its acid addition salts as well as the use of these chemical compounds in the treatment of vascular diseases and pharmaceutical compositions containing the said compounds as active ingredients.

BACKGROUND ART

The racemic 5,6-dihydro-5-(1-piperidinyl)-methyl-3-(3-pyridyl)4H-1,2,4-oxadiazine is known. Its preparation and hsp expression enhancing effect on cells exposed to heat shock is described in WO 97/16349 and its protective and regenerating effect on vascular endothelial cells is described in WO 98/06400. This compound is suitable mainly for fending off the damages caused by ischemia and in the treatment of cardiovascular and cerebrovascular diseases.

The optically active forms of 5,6-dihydro-5-(1-piperidinyl)-methyl-3-(3-pyridyl)-4H-1,2,4-oxadiazine were not described in the literature.

During our recent experiments, the optically active forms of 5,6-dihydro-5-(1-piperidinyl)-methyl-3-(3-pyridyl)4H-1,2,4-oxadiazine were prepared and their biological activities studied. It has been found that the (−)-5,6-dihydro-5-(1-piperidinyl)-methyl-3-(3-pyridyl)4H-1,2,4-oxadiazine has a substantially stronger vasoprotective and cardioprotective effect than the (+) enantiomer and the racemic compound. It is expressly more efficient in preventing the damages of the endothelium caused by ischemia.

Due to these properties the (−)-5,6-dihydro-5-(1-piperidinyl)-methyl-3-(3-pyridyl)4H-1,2,4-oxadiazine is prominently suitable to the treatment of vascular diseases and diseases connected to vascular abnormalities.

DISCLOSURE OF INVENTION

In course of experiments we recognized, unexpectedly, that (−)-5,6-dihydro-5-(1-piperidinyl)-methyl-3-(3-pyridyl)4H-1,2,4-oxadiazine, in contrast to the (+)-enantiomer and the racemic compound, has a positive inotropic effect i. e. it is capable of increasing the contractile force of the heart. This activity makes (−)-5,6-dihydro-5-(1-piperidinyl)-methyl-3-(3-pyridyl)4H-1,2,4-oxadiazine suitable for the treatment of patients with cardiac failure, contrary to the (+)-enantiomer and the racemic compound, the application of which being risky in case of cardiac failure.

BEST MADE OF CARRYING OUT THE INVENTION

The above mentioned advantageous biological properties of (−)-5,6-dihydro-5-(1-piperidinyl)-methyl-3-(3-pyridyl)-4H-1,2,4-oxadiazine are verified in the following tests.

Langendorff Perfused Rat Heart

Protocol for Assesment of Endothelial Function Before and After Ischemia

Rats were heparinised with i.p. heparin sodium (2500 IU) and anesthetized with i.p. pentobarbital (60 mg/kg). Hearts from spontaneously hypertensive (SH) rats were quickly removed and immediately perfused via the aorta using a gravity-flow, non-recirculating Langendorff apparatus (Experimetria Ltd) at a constant perfusion pressure (100 cm $H_2O$) with Krebs-Henseleit Solution (KHS) containing in mM: NaCl 120; KCl 5.4; $CaCl_2$ 2.7; $MgCl_2$ 1.1; $NaHCO_3$ 24; D-glucose 11. The KHS was gassed with carbogen (95% $O_2$; 5% $CO_2$) resulting pH 7.4.

We used the so-called non-working heart model and measured the mean coronary flow by a transonic flow meter (Type T206, Transonic Systems Inc.). The flow probe was placed above the aortic cannula. Coronary flow was monitored throughout the experiment and registered by a potentiometric recorder. Hearts were allowed to beat spontaneously throughout the experiment. After 20–30 min of equilibration period the coronary flow reached a baseline value.

Endothelial function was assessed through observations of preischemic and postischemic coronary flow responses to serotonin (5-HT). In response to serotonin, the progress of dilatation of coronary artery depends on the soundness of the endothelium.

The Langendorff infusion was switched to the another column containing additional $10^{-7}$ M serotonin (5-HT, Sigma Chemical Co.). The ensuing dilatation of coronary artery was monitored and when the steady state had been reached the 5-HT was washed out by switching back to the ordinary KHS. The heart was then subjected to a global ischemia for 10 min by the clamping the aortic cannula. At the end of the ischemic period, the heart was reperfused. When the baseline coronary flow had been reestablished, the heart was again subjected to the same protocol of sequential infusion of 5-HT and KHS as in the preischemic period. Control hearts were perfused with pure KHS and the hearts of the another three groups were perfused with KHS containing additional $10^{-6}$ M racemic 5,6-dihydro-5-(1-piperidinyl)-methyl-3-(3-pyridyl)4H-1,2,4-oxadiazine, (−)-5,6-dihydro-5-(1-piperidinyl)-methyl-3-(3-pyridyl)4H-1,2,4-oxadiazine and (+)-5,6-dihydro-5-(1-piperidinyl)-methyl-3-(3-pyridyl)4H-1,2,4-oxadiazine, respectively. 20–30 min after the onset of hemodynamic stability, perfusion of the drugs were initiated and continued until reperfusion with the exception of the occlusion period.

The results are shown in the following table. The potischemic coronary responses are expressed in percentage of the preischemic vasodilator responses.

| SH control | racemic compound | (−) enantiomer | (+) enantiomer |
|---|---|---|---|
| 37.13 ± 9.5 | 63.08 ± 11.7 p = 0.07 | 88.41 ± 10.9 p = 0.016 | 49.78 ± 9.9 p = 0.45 |

Perfusion of the rat heart with the (−)-5,6-dihydro-5-(1-piperidinyl)-methyl-3-(3-pyridyl)4H-1,2,4-oxadiazine ($10^{-6}$ M) preserved endothelial function after 10 min of global ischemia in contrast with the racemic compound, the (+) enantiomer and the racemic compound or the SH control.

Myocardial Infarction in Spontaneously Hypertensive Rats

Induction of Infarction

Myocardial ischemia was induced by a temporary occlusion of the main left coronary artery, according to Griswold et al (J. Pharmacol. Methods 1988, 20: 225–235). SH rats were anaesthetized with sodium pentobarbital (60 mg/kg i.p.). After tracheotomy, the animals were ventilated with room air by a respirator for small rodents (model: Harvard 552), with a stroke volume of 1,5–2 ml/100 g and a rate of 55 strokes/min to maintain normal $pO_2$, $pCO_2$ and pH parameters. The right carotid artery was catheterized and connected to a pressure transducer (P236B Stetham) for the measurement of systemic arterial blood pressure (BP) by means of a preamplifier (Hg-O2D Experimetria®). Heart rate (HR) was measured by a cardiotachometer (HR-01, Experimetria®). The electrocardiogram (ECG standard lead III) was recorded on a devices recorder (ER- 14, Micromed®) by means of subcutaneous steel needle electrodes. The chest was opened by a left thoracotomy and the heart was exteriorized by a gentle pressure on the right side of the rib cage. A 4/0 silk ligature was quickly placed under the main left coronary artery. The heart was replaced in the chest and the animal left to recover. Rectal temperature was monitored and was maintained constant at 37° C. The experiment was initiated with a 15 min stabilization period during which the observation of a sustained blood pressure less than 70 mmHg and/or the occurrence of arrhythmias lead to exclusion. Myocardial ischemia was induced with coronary artery occlusion for 1 h and reperfusion allowed for 1 hour. The drugs were administered orally 6 hours before occlusion.

Quantification of Myocardial Infarction

At the end of experiment, the heart was quickly removed. The left ventricle was then sliced into 2 mm thick sections parallel to the atrioventricular groove. The slices were incubated in a 0.1% solution of p-Nitroblue Tetrazolium (NBT) grade III, pH 7,4 for 15 min. The non-infarcted area was colored blue due to formation of a precipitate that results from reaction of NBT with dehydrogenase enzymes. Loss of these enzymes in the infarcted myocardium prevents the formation of the precipitate; thus, the infarcted area within the risk region remains pale yellow. The necrotic area was determined using computerized image analysis (COLIM, Pictron Kft), and was expressed as a percentage of the left ventricle.

| Groups | Infarcted area (%) | Survival (%) |
|---|---|---|
| SH control<br>n = 11 | 44.7 ± 2.5 | 54.5 |
| Treated with racemic compound<br>n = 10 | 27.2 ± 5.8** | 70.0 |
| Treated with (−) enantiomer<br>n = 10 | 7.1 ± 2.5** | 100.0** |
| Teated with (+) enantiomer<br>n = 10 | 34.5 ± 4.6 | 75.0 |

$p < 0.01$

Results

Acute single oral treatment with the (−) enantiomer (100 mg/kg) 6 hours before occlusion significantly reduced myocardial infarct size and increased survival rate in contrast with the (+) enantiomer in SH rats. It could be stated that the (−) enantiomer was more active in this model than the racemic compound or the (+) enantiomer.

Effect of racemic 5,6-dihydro-5-(1-piperidinyl)-methyl-3-(3-pyridyl)4H-1,2,4-oxadiazine and its (−) and (+) enantiomers on the contractile force of heart Materials and Methods New Zealand white rabbits (male, 2–3 kg) were killed by a blow on the nape. The hearts were rapidly removed after opening the chest. Right ventricular papillary muscles were dissected and mounted in organ holding chambers and pre-tension of 0.5 g was applied. The superfusate contained (in mM) 120 NaCl, 5.4 KCl, 2.7 $CaCl_2$, 1.1 $MgCl_2$, 1.1 $NaH_2PO_4$, 24.0 $NaHCO_3$ and 11.0 glucose. The pH of this superfusate was 7.4 at 37° C. when gassed with 95% $O_2$ and 5% $CO_2$. Stimulation and measurements were carried out by Isosys System of Experimetria, Budapest, Hungary. The preparations were paced by 1-ms-wide isolated constant voltage at a cycle length of 1000 ms. The amplitudes of the pulses were equal to twice as high as the diastolic threshold value, delivered through a pair of platinum electrodes. Before the start of the measurements the preparation was equilibrated for 60 min to allow the stabilization of its mechanical parameters. The drugs were added to the organ bath cumulatively, without washing out. Period of the incubation was 15–20 min. Measured parameters were: resting force (mg) and changes in the amplitude of contractile force (mg) which was expressed in % of the control.

| Concentration (M) | Racemic amplitude % | (−) enantiomer amplitude % | (+) enantiomer amplitude % |
|---|---|---|---|
| control | 100 | 100 | 100 |
| $10^{-6}$ | 92.6 ± 5.08 | 126.6 ± 5.3** | 90.1 ± 3.5 |
| $10^{-5}$ | 87.1 ± 3.5** | 132.8 ± 5.0** | 79.5 ± 5.6** |
| $10^{-4}$ | 83.7 ± 3.3** | 142.5 ± 4.8** | 78.4 ± 5.0** |

**$p < 0.01$

Results

The (−)-5,6-dihydro-5-(1-piperidinyl)-methyl-3-(3-pyridyl)4H-1,2,4-oxadiazine has a positive inotropic effect in rabbit papillary muscle between $10^{-6}$ and $10^{-4}$ molar range, the (+) enantiomer and the racemic compound showed a negative inotropic effect. Depression of left ventricular contractility is an unwanted effect sufficient to contraindicate its use in patients with overt cardiac failure.

The (−)-5,6dihydro-5-(1-piperidinyl)-methyl-3-(3-pyridyl)4H-1,2,4-oxadiazine can be prepared from the racemic compound. The racemic compound can be prepared for example by halogenating N-[2-hydroxy-3-(I-piperidinyl)-propoxy]-3-pyridine-carboximidamide and ring closure of the halogenated compound. In the first step the said starting compound is reacted with an inorganic halogenating agent, preferably thionyl chloride optionally in an inert solvent, and the excess of the reagent is removed for example by evaporation. The N-[2-halo-3-(1-piperidinyl)-propoxy]-3-pyridine-carboximidamide thus obtained is (optionally after isolation and purification) cyclised with a strong base, for example potassium tert. butylate, resulting in the desired racemic 5,6-dihydro-5-(1-piperidinyl)-methyl-3-(3-pyridyl) 4H-1,2,4-oxadiazine.

The resolution of the racemic compound can be accomplished by forming diastereomer salts. Preferably optically active (−)-L-dibenzoyl tartaric acid is used for the resolution. The salts are formed in an appropriate polar solvent, preferably methanol or in a mixture of methanol and water then the isolated salt enriched in the desired diastereomer is recrystallized from the same or a similar solvent for further purification. The progress of purification is expediently monitored by HPLC chromatography with use of a chiral sorbent. When the desired purity is attained the base is liberated simply by alkalinization or alkaline extraction and isolated by recrystallization.

The (−)-5,6-dihydro-5-(1-piperidinyl)-methyl-3-(3-pyridyl)AH-1,2,4-oxadiazine thus obtained can be used as a base or optionally can be converted into an acid addition salt appropriate to the particular application. For this purpose the base is reacted with an inorganic or organic acid in a known manner. The (−)-5,6-dihydro-5-(1-piperidinyl)-methyl-3-(3-pyridyl)4H-1,2,4-oxadiazine base and the acid addition salts are one of the objects of the invention.

According to the invention these compounds are used in the treatment and prevention of vascular diseases and diseases connected to vascular abnormalities.

According to a special embodiment of the invention these compounds are applied in the treatment and prevention of vascular diseases and diseases connected to vascular abnormalities on patients with cardiac failure.

The compounds of the invention can be used both in the human therapy and in the veterinary practice.

Accordingly, in a further aspect, the invention relates to a method of treatment and prevention of vascular diseases and diseases connected with vascular abnormalities comprising administering to the patient (−)-5,6-dihydro-5-(1-piperidinyl)-methyl-3-(3-pyridyl)4H-1,2,4-oxadiazine or an acid addition salt thereof. In a preferred embodiment case of the invention, (−)-5,6-dihydro-5-(1-piperidinyl)-methyl-3-(3-pyridyl)4H-1,2,4-oxadiazine or an acid addition salt thereof is administered to a patient suffering in cardiac failure.

The dose of the compounds of the invention depends on the patient and the disease and varies from 0.1 to 200 mg/kg/day, preferably from 0.1 to 50 mg/kg/day. For human therapy the preferred oral dose is 10–200 mg, in case of rectal administration 1–15 mg and in case of parenteral treatment 2–20 mg for an adult daily. These doses are applied in unit dosage forms optionally distributed to 2–3 administrations, particularly in case of oral treatment.

The invention relates further to the pharmaceutical compositions usable to the treatment. The parmaceutical compositions of the invention comprise (−)-5,6-dihydro-5-(1-pipenidinyl)-methyl-3-(3-pyridyl)4H-1,2,4-oxadiazine or an acid addition salt thereof as active ingredient with carriers and auxiliary materials conventionally used in the pharmaceutical compositions.

The compositions of the invention can be formulated in solid or liquid forms usually applied in the human and veterinary therapy. For oral use tablets, coated tablets, dragees, granules, capsules, solutions or syrups, for rectal administration suppositories and for parenteral administraton lyophilised or non-lyophilised injectables or infusion solutions can be prepared with use of known ways of preparation. The oral compositions may comprise fillers such as microcrystalline cellulose, starch, lactose, lubricants, such as stearic acid and magnesium stearate, coating materials such as sugar, film materials such as hydroxymethyl cellulose, flavours or sweeteners such as methyl paraben and saccharine and colorants. The auxiliaries in suppositories may be for example cocoa bufter and polyethylene glycol. The compositions for parenteral use may comprise saline or optionally dispersing and wetting agents such as propylene glycol with the active ingredient.

The invention is illustrated in the following examples.

EXAMPLE 1

Preparation of (−)-5,6-dihydro-5-(1-piperidinyl)-methyl-3-(3-pyridyl)4H-1,2,4-oxadiazine 19.7 g (0.076 mol) of 5,6-dihydro-5-(1-piperidinyl)-methyl-3-(3-pyridyl)4H-1,2,4-oxadiazine was dissolved in 300 ml methanol and 28.5 g (0.076 mol) (−)-L-dibenzoyl tartaric acid monohydrate were added. When the dissolution was complete crystallization was initiated and the suspension was kept in refrigerator over night. The precipitated crystalline material was filtered, washed and dried. 23.2 g of product was obtained with a melting point of 159–160° C.

The salt thus obtained was recrystallized from hot methanol. The weight of the precipitated material was 7.9 g.

From the dibenzoyl tartaric acidic salt (7.9 g) the base was liberated with 130 ml 1 M aqueous sodium carbonate solution and extracted with 2×130 ml choloroform. The organic layer was dried over sodium sulphate, filtered and evaporated. The raw base (3.2 g) was recrystallized from 41 ml ethyl acetate. The precipitate was filtered and dried. 2.55 g title product is obtained. Mp: 137–140° C.

$[\alpha]_{406}$=72° (c=1, DMF)

Optical purity: 97,6 % (HPLC)

IR (KBr, cm$^{-1}$): 3185 (b), 2912, 2890 (b), 1603, 1570, 1460, 1335, 1128, 975, 857, 801, 694.

$^1$H-NMR (250 MHz, solvent: CDCl$_3$, ref.: CHCl$_3$ δ/ppm/): 8.88 (1H, dd), 8.68 (1H, dd), 8.00 (1H, ddd), 7.36 (1H, ddd): pyridine; 5.8 (1H, s/br): NH; 4,24 (1H, dd), 3.45 (1H, dd): OCH$_2$; 3.82 (1H, m): N—CH—N; 2.3–2.7 (6H, m): 3×NCH$_2$; 1.75–1.4 (6H, m): 3×piperidine CH$_2$.

$^{13}$C-NMR (63 MHz, solvent: CDCl$_3$, ref.: CDCl$_3$=77.0 ppm, δ/ppm/): 167.0 (COOH); 150.9, 128.5, 133.4, 123.3, 146.7 (pyridine 2-3-4-5-6); 150.9 (C=NO); 67.1 (NOCH$_2$); 59.5 (CH$_2$NH); 46.2 (NCH); 54.7, 26.0, 24.1 (piperidine).

Determination of optical purity with HPLC, chromatographic conditions:

column: stainless stell, 250×4.6 mm packed with CHIRALCEL OC temperature: 40° C.

mobil phase: mixture of 500 ml of ethanol and 500 ml of n-hexane flow rate: 0,5 ml/min detection: UV 220 nm approximate retention times:
(−) enantiomer: 14 min
(+) enantiomer: 16 min

EXAMPLE 2

(−)-5,6-dihydro-5-(1-piperidinyl)-methyl-3-(3-pyridyl)-4H-1,2,4-oxadiazine hydrochloride 390 mg (1.5 mmol) of compound of Example 1 was dissolved in 4 ml ethyl acetate. 0.4 ml of 3.7 M hydrochloric acid was added. Dissoluton was promoted by the addition of 1.0 ml methanol then the solution was evaporated to dryness. The residue (540 mg) was crystallized from a mixture of methanol and diethyl ether while cooling in refrigerator. 280 mg (69.2 %) product was obtained. Mp.: 150–153° C.

IR (KBr, cm$^{-1}$): 3177, 2930, 2622, 2531, 1608, 1533, 1463, 1185, 1117, 1026, 950, 799, 716.

EXAMPLE 3

(−)-5,6-dihydro-5-(1-piperidinyl)-methyl-3-(3-pyridyl)-4H-1,2,4-oxadiazine maleate 390 mg (1.5 mmol) of compound of Example 1 was dissolved in 4 ml of hot i-propyl alcohol. 0.174 g maleic acid was added and dissolved while heating, then the solution was evaporated to dryness. The residue (620 mg) was crystallized from 2.0 ml of ethyl acetate while cooling, then filtered and washed with ethyl acetate. 520 mg (69.2%) product was obtained. Mp.: 127–130° C.

IR (KBr, cm$^{-1}$): 3257, 2941, 2673, 2561, 1690, 1362, 1197, 1100, 946, 866, 819, 721.

EXAMPLE 4

| Tablets | |
|---|---|
| (−)-5,6-dihydro-5-(1-piperidinyl)-methyl-3-(3-pyridyl)-4H-1,2,4-oxadiazine | 20.0 mg |
| corn starch | 100.0 mg |
| lactose | 95.0 mg |
| talc | 4.5 mg |
| magnesium stearate | 0.5 mg |

The active compound was finely ground, mixed with the excipients, the mixture was homogenized and granulated. The granulate was pressed into tablets.

EXAMPLE 5

| Capsules | |
|---|---|
| (−)-5,6-dihydro-5-(1-piperidinyl)-methyl-3-(3-pyridyl)-4H-1,2,4-oxadiazine sulphate | 20.0 mg |
| microcrystalline cellullose | 99.0 mg |
| amorphous silica | 1.0 mg |

The active ingredient was mixed with the additives, the mixture was homogenized and filled into gelatine capsules.

EXAMPLE 6

| Dragees | |
|---|---|
| (−)-5,6-dihydro-5-(1-piperidinyl)-methyl-3-(3-pyridyl)-4H-1,2,4-oxadiazine hydrobromide | 25.0 mg |
| lactose | 82.5 mg |
| potatoe starch | 33.0 mg |
| polivinyl pyrrolidone | 4.0 mg |
| magnesium stearate | 0.5 mg |

The active ingredient and the polyvinyl pyrrolidone were dissolved in ethanol. The lactose and the potatoe starch were mixed and the mixture was evenly wetted with the granulating solution of the active ingredient. After sieving the humid granulate was dried at 50° C. and sieved. Magnesium stearate was added and the granulate was pressed into dragée cores. The cores were coated by sugar and polished with bee wax.

EXAMPLE 7

| Suppositories | |
|---|---|
| (−)-5,6-dihydro-5-(1-piperidinyl)-methyl-3-(3-pyridyl)-4H-1,2,4-oxadiazine fumarate | 4.0 mg |
| cocoa butter | 3.5 g |
| solid fat 50 suppository mass | 15.0 g |

The cocoa butter and the suppository mass were heated to 40° C. and the active ingredient was dispersed in the melt. The mass was cast in suppository forms.

EXAMPLE 8

| Solution | |
|---|---|
| (−)-5,6-dihydro-5-(1-piperidinyl)-methyl-3-(3-pyridyl)-4H-1,2,4-oxadiazine hydrochloride | 500 mg |
| sorbite | 10 g |
| saccharin sodium | 0.05 g |
| twice distilled water | q.s. ad 100 ml |

EXAMPLE 9

| Injecton vial | |
|---|---|
| (−)-5,6-dihydro-5-(1-piperidinyl)-methyl-3-(3-pyridyl)-4H-1,2,4-oxadiazine maleate | 2 mg |
| physiological saline solution, pyrogen-free, sterile | q.s. ad 2.0 ml |

The solution is filled in vials and the vials are sealed.

EXAMPLE 10

Infusion solution

Infusion solution of 500 ml volume was prepared with the following composition:

| | |
|---|---|
| (−)-5,6-dihydro-5-(1-piperidinyl)-methyl-3-(3-pyridyl)-4H-1,2,4-oxadiazine methansulphonate | 20 mg |
| physiological saline solution, pyrogen-free, sterile | q.s. ad 500 ml |

What is claimed is:

1. (−)-5,6-dihydro-5-(1-piperidinyl)-methyl-3-(3-pyridyl)-4H-1,2,4-oxadiazine and its acid addition salts.

2. A method of affecting the vasoprotective activity in the treatment of at least one disease chosen from vascular diseases and diseases connected to vascular abnormalities comprising administering to the patent an effective dosage of (−)-5,6-dihydro-5-(1-piperidinyl)-methyl-3-(3-pyridyl)-4H-1,2,4-oxadiazine or an acid addition salt thereof.

3. A method according to claim 2, wherein said (−)-5,6-dihydro-5-(1-piperidinyl)-methyl-3-(3-pyridyl)-4H-1,2,4-oxadiazine or an acid addition salt thereof is administered to a patient in cardiac failure.

4. A pharmaceutical composition having a vasoprotective activity comprising a pharmaceutical carrier and an effective amount of (−)-5,6,-dihydro-5-(1-piperidinyl)-methyl-3-(3-pyridyl)4H-1,2,4-oxadiazine or an acid addition salt thereof.

5. A method of affecting the cardioprotective activity in the treatment of at least one disease chosen from vascular diseases and diseases connected to vascular abnormalities comprising administering to the patent an effective dosage of (−) 5,6-dihydro-5-(1-piperidinyl)-methyl-3-(3-pyridyl)-4H-1,2,4-oxadiazine or an acid addition salt, thereof.

6. A method according to claim 5, wherein said (−)-5,6-dihydro-5-(1-piperidinyl)-methyl-3-(3-pyridyl)-4H-1,2,4-oxadiazine or an acid addition salt thereof, is administered to a patient in cardiac failure.

7. A pharmaceutical composition having a cardioprotective activity comprising a pharmaceutical carrier and an effective amount of (−)-5,6,-dihydro-5-(1-piperidinyl)-methyl-3-(3-pyridyl)4H-1 ,2,4-oxadiazine or an acid addition salt thereof.

8. A pharmaceutical composition according to claim 4, further comprising auxiliaries conventionally used in pharmaceutical compositions.

9. A pharmaceutical composition according to claim 7, further comprising auxiliaries conventionally used in pharmaceutical compositions.

10. A method of affecting the vasoprotective activity in the prevention of at least one disease chosen from vascular diseases and diseases connected to vascular abnormalities comprising administering to the patient an effective dosage of (−)-5,6-dihydro-5-(1-piperidinyl)-methyl-3-(3-pyridyl)-4 H-1,2,4-oxadiazine or an acid addition salt, thereof.

11. A method of affecting the cardioprotective activity in the prevention of at least one disease chosen from vascular diseases and diseases connected to vascular abnormalities comprising administering to the patent an effective dosage of (−)-5,6-dihydro-5-(1-piperidinyl)-methyl-3-(3-pyridyl)-4H-1,2,4-oxadiazine or an acid addition salt thereof.

12. A method according to claim 10, wherein said (−)-5,6-dihydro-5-(1-piperidinyl)-methyl-3-(3-pyridyl)-4H-1,2,4-oxadiazine or an acid addition salt thereof is administered to a patient in cardiac failure.

13. A method according to claim 12, wherein said (−)-5,6-dihydro-5-(1-piperidinyl)-methyl-3-(3-pyridyl)4H-1,2,4-oxadiazine or an acid addition salt thereof is administered to a patient in cardiac failure.

\* \* \* \* \*

UNITED STATES PATENT AND TRADEMARK OFFICE
CERTIFICATE OF CORRECTION

PATENT NO. : 6,384,029 B1 Page 1 of 1
DATED : May 7, 2002
INVENTOR(S) : Jednákovits et al.

It is certified that error appears in the above-identified patent and that said Letters Patent is hereby corrected as shown below:

<u>Title page,</u>
Item [54], title "OXDADIAZINE" should read -- OXADIAZINE --.

Item [57], ABSTRACT,
Line 3, "phamaceutical" should read -- pharmaceutical --.
Line 4, "compounds" should read -- compound --.

<u>Column 8,</u>
line 39, "patent" should read -- patient --.
Line 49, "pyridyl)4H-" should read --pyridyl)-4H- --.
Line 53, "patent" should read -- patient --.
Line 54, "(-) 5,6-dihydro-" should read -- (-)-5,6-dihydro- --.
Line 63, "(3-pyridyl)4H-1, 2,4-oxadiazine" should
read -- (3-pyridyl)-4H-1,2,4-oxadiazine --.

<u>Column 9,</u>
Line 9, "pyridyl )-4 H-" should read --pyridyl)-4H- --.
Line 14, "patent" should read -- patient --.

<u>Column 10,</u>
Line 8, "(3-pyridyl)4H-1,2,4-" should read -- (3-pyridyl)-4H-1,2,4- --.

Signed and Sealed this

Twenty-sixth Day of November, 2002

*Attest:*

JAMES E. ROGAN
*Attesting Officer*     *Director of the United States Patent and Trademark Office*